United States Patent [19]

Terrell et al.

[11] Patent Number: 4,943,502
[45] Date of Patent: Jul. 24, 1990

[54] PHOTOSENSITIVE RECORDING MATERIAL SUITED FOR USE IN ELECTROPHOTOGRAPHY CONTAINING DIHYDROQUINOLINE CHARGE TRANSPORT COMPOUNDS

[75] Inventors: David R. Terrell, Lint; Marcel J. Monbaliu, Mortsel, both of Belgium; Ulrich Grigo, Kempen; Klaus Berg, Krefeld, both of Fed. Rep. of Germany

[73] Assignee: Agfa-Gevaert, N.V., Mortsel, Belgium

[21] Appl. No.: 360,303

[22] Filed: Jun. 2, 1989

[30] Foreign Application Priority Data

Jun. 23, 1988 [EP] European Pat. Off. ........ 88201293.3

[51] Int. Cl.⁵ ............................................. G03G 5/14
[52] U.S. Cl. ....................................... 430/58; 546/61; 546/180; 546/152; 546/178; 546/176
[58] Field of Search ...................... 430/58, 59; 546/61, 546/180, 176

[56] References Cited

U.S. PATENT DOCUMENTS 4,481,272 11/1984 Eckell et al. ........................ 430/58

Primary Examiner—J. David Welsh
Attorney, Agent, or Firm—A. W. Breiner

[57] ABSTRACT

An electrophotographic recording material which comprises an electrically conductive support having thereon a double layer of a charge generating layer in contiguous relationship with a charge transporting layer comprising a positive charge transporting compound corresponding to the following general formula (I):

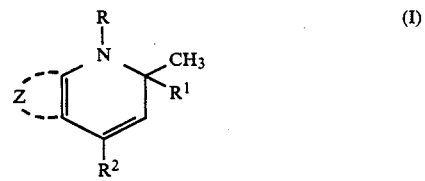

wherein:
R represents hydrogen or an aliphatic or cycloaliphatic group including these groups substituted by non-ionic substituents,
each of $R^1$ and $R^2$ (same or different) represents a $C_1$-$C_6$ alkyl group or an aryl group, and
Z represents the atoms necessary to close an adjacent aromatic nucleus or aromatic ring system including such nucleus or ring system substituted with one or more substituents of non-ionic character.

12 Claims, No Drawings

PHOTOSENSITIVE RECORDING MATERIAL SUITED FOR USE IN ELECTROPHOTOGRAPHY CONTAINING DIHYDROQUINOLINE CHARGE TRANSPORT COMPOUNDS

The present invention relates to a photosensitive recording material suited for use in electrophotography.

In electrophotography photoconductive materials are used to form a latent electrostatic charge image that is developable with finely divided colouring material, called toner.

The developed image can then be permanently affixed to the photoconductive recording material. e.g. photoconductive zinc oxide-binder layer, or transferred from the photoconductor layer, e.g. selenium layer, onto a receptor material. e.g. plain paper and fixed thereon. In electrophotographic copying and printing systems with toner transfer to a receptor material the photoconductive recording material is reusable. In order to permit a rapid multiple printing or copying a photoconductor layer has to be used that rapidly looses its charge on photo-exposure and also rapidly regains its insulating state after the exposure to receive again a sufficiently high electrostatic charge for a next image formation. The failure of a material to return completely to its relatively insulating state prior to succeeding charging/imaging steps is commonly known in the art as "fatigue".

The fatigue phenomenon has been used as a guide in the selection of commercially useful photoconductive materials, since the fatigue of the photoconductive layer limits the copying rates achievable.

Another important property which determines whether or not a particular photoconductive material is suited for electrophotographic copying is its photosensitivity that must be high enough for use in copying apparatus operating with a copying light source of fairly low intensity.

Commercial usefulness further requires that the photoconductive layer has a chromatic sensitivity that matches the wavelength(s) of the light of the light source, e.g. laser or has panchromatic sensitivity when white light is used e.g. to allow the reproduction of all colours in balance.

Intensive efforts have been made to satisfy said requirements, e.g. the spectral sensitivity of selenium has been extended to the longer wavelengths of the visible spectrum by making alloys of selenium, tellurium and arsenic. In fact selenium-based photoconductors remained for a long time the only really useful photoconductors although many organic photoconductors were discovered.

Organic photoconductor layers of which poly(N-vinylcarbazole) layers have been the most useful were less interesting because of lack of speed, insufficient spectral sensitivity and rather large fatigue.

However, the discovery that 2,4 7-trinitro-9-fluorenone (TNF) in poly(N-vinylcarbazole) (PVCz) formed a charge-transfer complex strongly improving the photosensitivity (ref. U.S. Pat. No. 3,484,237) has opened the way for the use of organic photoconductors in copying machines that could compete with the selenium-based machines.

TNF acts as an electron acceptor whereas PVCz serves as electron donor. Films consisting of said charge transfer complex with TNF:PVCz in 1:1 molar ratio are dark brown, nearly black and exhibit high charge acceptance and low dark decay rates. Overall photosensitivity is comparable to that of amorphous selenium (ref. Schaffert, R. M. IBM J. Res. Develop. 15, 75 (1971).

A further search led to the discovery of phthalocyanine-binder layers, using poly(N-vinylcarbazole) as the binder [ref. Hackett, C. F., J. Chem. Phys.. 55, 3178 (1971)]. The phthalocyanine was used in the metal-free X form and according to one embodiment applied in a multilayer structure wherein a thin layer of said phtalocyanine was overcoated with a PVCz layer. Hackett found that photoconductivity was due to field dependent photogeneration of electron-hole pairs in the phthalocyanine and hole injection into the PVCz. The transport of the positive charges, i.e. positive hole conduction proceeded easily in the PVCz layer. From that time on much research has been devoted to developing improved photoconductive systems wherein charge generation and charge transport materials are separate in two contiguous layers (see e.g. U.K. Pat. No. 1,577,859). The charge generating layer may be applied underneath or on top of the charge transport layer. For practical reasons, such as less sensitivity to wear and ease of manufacture, the first mentioned arrangement is preferred wherein the charge generating layer is sandwiched between a conductive support and a light transparent charge transport layer (ref. Wolfgang Wiedemann, Organische Photoleiter - Ein Uberblick, II. Chemiker Zeitung. 106. {1982) Nr. 9 p. 315).

In order to form a photoconductive two layer-system with high photosensitivity to the visible light dyes having the property of photo-induced charge generation have been selected. Preference is given to a water-insoluble pigment dye of e.g. one of the following classes:

(a) perylimides, e.g. C.I. 71 130 (C.I.=Colour Index) described in DBP No. 2 237 539, (b) polynuclear quinones. e.g. anthanthrones such as C.I. 59 300 described in DBP No. 2 237 678, (c) quinacridones, e.g. C.I. 46 500 described in DBP No. 2 237 679, (d) naphthalene 1,4.5,8-tetracarboxylic acid derived pigments including the perinones, e.g. Orange GR, C. I. 71 105 described in DBP No. 2 239 923, (e) phthalocyanines, e.g. H$_2$-phthalocyanine in X-crystal form (X-H$_2$Ph), metal phthalocyanines, e.g. CuPc C.I. 74 160 described in DBP No. 2 239 924 and indium phthalocyanine described in U.S. Pat. No. 4,713,312, (f) indigo- and thioindigo dyes, e.g. Pigment Red 88, C.I. 73 312 described in DBP No. 2 237 680, (g) benzothioxanthene-derivatives as described e.g. in DAS No. 2 355 075.

(h) perylene 3,4,9,10-tetracarboxylic acid derived pigments including condensation products with o-diamines as described e.g. in DAS No. 2 314 051, (i) polyazo-pigments including bisazo-, trisazo- and tetrakisazo-pigments, e.g. Chlordiane Blue C.I. 21 180 described in DAS No. 2 635 887. and bisazopigments described in DOS No. 2 919 791, DOS No. 3 026 653 and DOS No. 3 032 117.

(j) squarilium dyes as described e.g. in DAS No. 2 401 220. (k) polymethine dyes.

(l) dyes containing quinazoline groups. e.g. as described in GB-P No. 1 416 602 according to the following general formula:

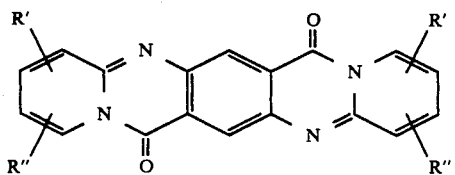

in which R' and R" are either identical or different and denote hydrogen, $C_1$–$C_4$ alkyl, alkoxy, halogen, nitro or hydroxyl or together denote a fused aromatic ring system.

(m) triarylmethane dyes, and (n) dyes containing 1,5 diamino-anthraquinone groups.

The charge transporting layer can comprise either a polymeric material or a nonpolymeric material. In the case of nonpolymeric materials the use of such materials with a polymeric binder is generally preferred or required for sufficient mechanical firmness and flexibility. This binder may be "electronically inert" (that is incapable of substantial transport of at least one species of charge carrier) or can be "electronically active" (capable of transport of that species of charge carriers that are neutralized by a uniformly applied electrostatic charge). For example, in the arrangement: conductive support-charge generating layer-charge transport layer, the polarity of electrostatic charging that gives the highest photosensitivity to the arrangement has to be such that negative charging is applied to a hole conducting (p-type) charge transport layer and positive charging is applied to an electron conducting (n-type) charge transport layer.

Since most of the organic pigment dyes of the charge generating layer provide more efficient hole injection than electron injection across a field-lowered barrier at the interface where pigment-dye/charge transport compounds touch each other and possibly form a charge transfer complex there is a need for charge transport materials that have a good positive hole transport capacity for providing an electrophotographic recording system with low fatigue and high photosensitivity.

According to the already mentioned article "Organische Photoleiter Ein Überblick; II of Wolfgang Wiedemann. p. 321. particularly efficient p-type transport compounds can be found in the group consisting of heteroaromatic compounds, hydrazone compounds and triphenylmethane derivatives. Examples of double layer systems containing hydrazone compounds as charge transporting substance are described in U.S. Pat. Nos. 4,278,747 and 4,365,014. Examples of triphenylmethane derivatives that are particularly useful as charge transporting compounds in a double layer photoconductive system are given in U.S. Pat. Nos. 4,140,529 and 4,330,608.

The use of triarylalkane organic photoconductors in single layer photoconductive materials was already known from U.S. Pat No. 3,542,544 coresponding to German Auslegeschrift (DAS) No. 1 237 900.

The use of photoconductive heteroaromatic compounds such as 1,2-dihydroquinoline compounds and 1,2,3,4-tetrahydroquinoline compounds in single layer photoconductive materials is described in U.S. Pat. Nos. 3,832,171, 3,830,647 and 3,798,031.

Compounds that are known for use as photoconductive materials in photoconductive single layer systems are not automatically particularly suited for use in the described two-layer system since such will be dependent on their capability of p-type charge transport which cannot be assessed by simply considering their chemical structure but has to be established by experiment using said photoconductive compounds in a layer in contiguous relationship with a charge generating layer that provides electron-positive hole pairs on photo-exposure.

For example photoconductive 1,2-bis(1,2,3,4,-tetrahydroquinolin-1-yl) ethane and 1,2-bis (1,2,3,4-tetrahydro-2,2,4-trimethyl-quinolin-1-yl)ethane described in U.S. Pat. No. 3,798,031 which showed the highest sensitivties in single layer photoconductive layers consisting of about 57% wt of said 1,2,3,4, -tetrahydroquinoline compounds applied in a vinyl chloride/vinyl acetate/ maleic anhydride terpolymer binder both exhibited only 3.3% discharge when evaluated in a two layer photoconductive recording material system consisting of an aluminium coated polyester film sequentially coated with a 0.6 $\mu$m thick charge generating layer consisting of 50% wt of X-phthalocyanine,45% wt of polycarbonate and 5% wt of polyester and a 15 $\mu$m thick charge transport layer consisting of 50% wt of the said 1,2,3,4-tetrahydroquinoline compounds in polycarbonate under the conditions which have been applied in Example 1 described herein.

It is an object of the present invention to provide a photoconductive composite layer material comprising a charge generating layer in contiguous relationship with a charge transport layer containing an organic photoconductive compound that has a particularly high p-type charge transport capacity.

It is another object of the present invention to provide a recording process wherein a charge pattern of negative charge polarity is formed on said composite layer material by negatively charging the charge transport layer containing an organic photoconductive compound and imagewise photo-exposing the charge generating layer that is in contiguous relationship with said charge transport layer.

Other objects and advantages of the present invention will appear from the further description and examples.

In accordance with the present invention an electrophotographic recording material is provided which comprises an electrically conductive support having thereon a charge generating layer in contiguous relationship with a charge transporting layer, characterized in that said charge transporting layer contains a 1;2-dihydroquinoline compound having preferably a melting point of at least 30° C., more preferably of at least 100° C., and corresponding to the following general formula (I):

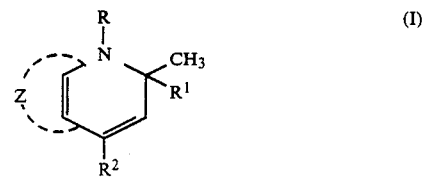

wherein:
R represents hydrogen or an aliphatic or cycloaliphatic group, e.g. a saturated aliphatic group or an unsaturated aliphatic group, including these groups substituted by non-ionic substituents.
each of $R^1$ and $R^2$ (same or different) represents a $C_1$–$C_6$ alkyl group, e.g. methyl, ethyl, n-propyl, iso-propyl, n-butyl, isobutyl, n-pentyl and n-hexyl, or an aryl group, e.g. phenyl, and Z represents the atoms necessary to close an adjacent aromatic nucleus, e.g. benzene nucleus, or aromatic ring system including such nucleus or ring system substituted with one or more substituents of non-ionic character, e.g. substituted with one or more alkyl groups, one or more halogen atoms, e.g. F, Cl, Br or I, one or more cyano groups, nitro groups, alkoxy groups, e.g. methoxy, or amino groups, e.g. a monoalkylamino or a dialkylamino group, (a) hydrazone group(s), e.g. (a) formyl-1,1-diphenyl hydrazone group, a formyl-1-methyl-1-phenyl hydrazone group, (an) azo group(s), e.g. an azobenzene group, (an) enamine groups, e.g. a group obtained by condensation of formaldehyde with a primary amine group.

The melting point of said positive charge transport compound is preferably at least 100° C. in order to prevent marked softening of the charge transport layer and diffusion of said compound out of the recording material at elevated temperature conditions.

The R substituent is preferably one that can be introduced by alkylation, for example an alkyl radical including a substituted alkyl radical, e.g. methyl, a cycloalkyl radical, e.g. cyclohexyl, an allyl radical or an aralkyl radical, e.g. benzyl.

The adjacent aromatic ring closed by the atoms represented by Z is preferably one of the following group: naphthalene, anthracene, carbazole, indole, benzofuran, benzothiophene, dibenzofuran, dibenzothiophene, phenothiazie, phenoxazine, indene, fluorene, xanthene anthraquinone and benzanthrone.

Preferred compounds for use according to the present invention are listed in Table 1 with their melting points and structural formula:

TABLE 1

| No. | Formula | Melting point (°C.) |
| --- | --- | --- |
| A | | 161 |
| B | | 133 |
| C | | 68 |

TABLE 1-continued

| No. | Formula | Melting point (°C.) |
|---|---|---|
| D | 1-benzyl-2,2,4,7-tetramethyl-1,2-dihydroquinoline | 78 |
| E | 1-benzyl-6-ethoxy-2,2,4-trimethyl-1,2-dihydroquinoline | 65 |
| F | 1,2,2,4-tetramethyl-6-(phenylazo)-1,2-dihydroquinoline | 72 |
| G | 2,2,4-trimethyl-2,9-dihydro-1H-indeno[2,1-b]quinoline | 169 |
| H | 6-[(2,2-diphenylhydrazono)methyl]-1,2,2,4-tetramethyl-1,2-dihydroquinoline | 156 |
| I | 6-{[2-methyl-2-phenylhydrazono]methyl}-1,2,2,4-tetramethyl-1,2-dihydroquinoline | 127 |

TABLE 1-continued

| No. | Formula | Melting point (°C.) |
|---|---|---|
| J | 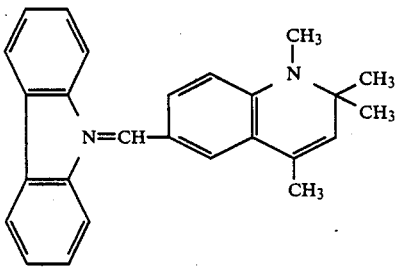 | 127 |

Other preferred 1,2-dihydroquinoline compounds are so-called "duplo-compounds" containing two 1,2-dihydroquinoline nuclei linked through their ring-nitrogen atoms by a bivalent organic group, these compounds being within the scope of the following general formula (II):

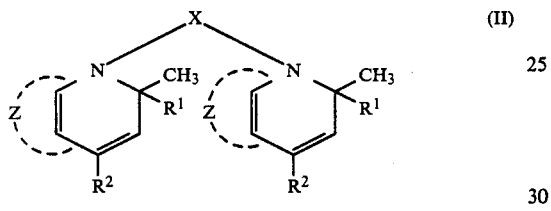   (II)

wherein:

X is a bivalent aliphatic or cycloaliphatic group, e.g. of the type that can be introduced by alkylation, e.g. an alkylene group, preferably an ethylene group, a substituted alkylene group or an alkylene chain interrupted by a bivalent aromatic group, e.g. a phenylene, naphthalene or anthracene group, or a bivalent aliphatic group wherein at least two carbon atoms are linked through a hetero-atom selected from the group consisting of oxygen, sulphur or nitrogen wherein nitrogen is substituted with a monovalent hydrocarbon group, e.g. an aryl group, and $R^1$ $R^2$ and Z have the same significance as described above. Specific examples of "duplo-compounds" suited for use according to the present invention are listed in Table 2 with their melting points.

TABLE 2

| No. | Formula | Melting point °C. |
|---|---|---|
| 1 | 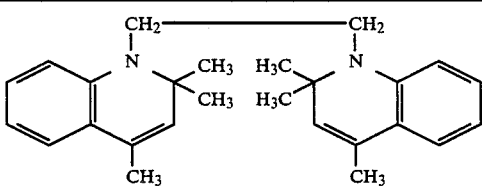 | 140 |
| 3 | 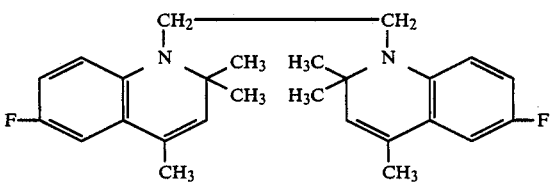 | 210 |
| 4 | 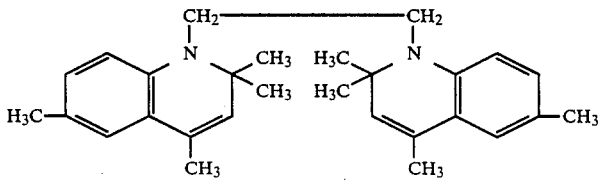 | 179 |
| 5 | 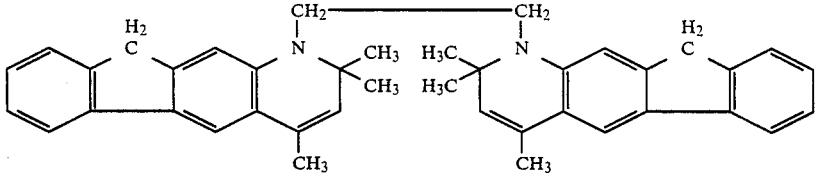 | 241 |

TABLE 2-continued

| No. | Formula | Melting point °C. |
|---|---|---|
| 6 | (structure) | 171 |
| 7 | (structure) | 129 |
| 8 | (structure) | 195 |
| 9 | (structure) | 109 |
| 10 | (structure) | 205 |
| 11 | (structure) | oil at room temp. |

TABLE 2-continued

| No. | Formula | Melting point °C. |
|---|---|---|
| 12 | (structure) | about 50 |
| 13 | (structure) | 180 |
| 14 | (structure) | 150 |
| 15 | (structure) | 147 |
| 16 | (structure) | 215 |
| 17 | (structure) | 186 |

The preparation of the intermediate 1,2-dihydro-2,2,4-trialkylquinolines in which R=H proceeds advan- The production of the intermediates wherein $R^1=R^2$ is illustrated by the following reaction scheme:

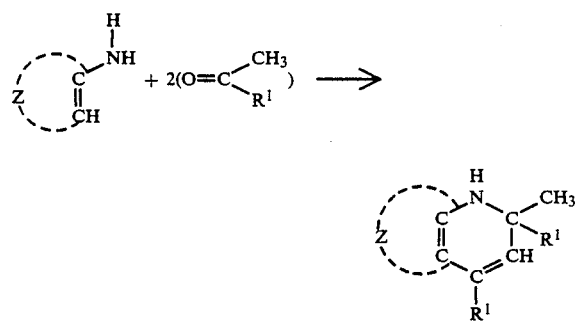

in which Z and $R^1$ have the same meaning as described above.

The preparation of the intermediate 1,2-dihydro-2-methyl-2,4-diphenyl-quinolines was described by A. Arduini. F. Bigi, G. Casiraghi, G. Casnati and G. Sartori in 1981 in Synthesis. pages 975-978 and proceeds advantageously by reacting an aromatic lithium primary amino compound with phenyl acetylene in the presence of tin tetrachloride. This is illustrated by the following reaction scheme:

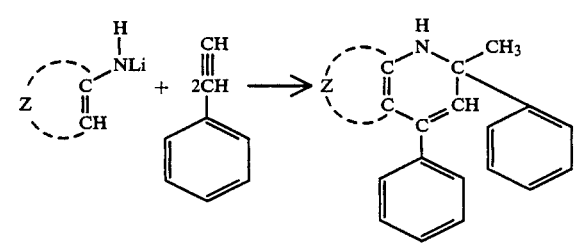

in which Z has the same meaning as described above.

The introduction of the substituent R replacing the hydrogen in the NH group of the 1,2-dihydroquinoline may proceed according to known alkylation techniques.

For introducing an alkyl substituent in the 1-position of the 1,2-dihydroquinoline any suitable alkylating agent e.g. trialkyl phosphates, alkyl sulfonates, alkyl iodides, alkyl bromides and alkyl chlorides may be used, the latter preferably in conjunction with a small amount of potassium iodide.

For illustrative purposes the preparation of compounds A and B mentioned hereinbefore is given.

PREPARATION OF COMPOUND A

A mixture of 15.66 g (0.06 mole) of 2,2,4-trimethyl-1,2-dihydro-10H-indeno[1,2-g]-quinoline and 6.9 ml of benzyl chloride (0.06 mole), 10.44 ml of diisopropylethylamine and 10 ml of dimethylacetamide were heated for 2 h at 120° C. After that period the reaction mixture was cooled down and 50 ml of methanol were added thereto. The obtained precipitate was separated by suction filtering. Yield of crude product: 17 g and melting point 160° C. After purification by column-chromatography 14.3 g of compound A melting at 161° C. were obtained.

PREPARATION OF COMPOUND B A mixture of 18 g (0.05 mole) of 1,3-dimethyl-2,5,6-tribromobenzene, 26 g (0.15 mole) of 2,2,4-trimethyl-1,2-dihydroquinoline, 26.5 ml of diisopropylethylamine and 100 ml of dimethylacetamide were heated for 3 h at 120° C. The obtained solution was poured into water and the crude product was extracted with diethyl ether. After drying and removal of the ether by evaporation the obtained product was purified by column-chromatography. Yield: 10 g. Melting point 133° C.

PREPARATION OF COMPOUND F 10.9 g (0117 mole) of aniline were dissolved in 30 ml of water and 30 ml of concentrated hydrochloric acid. At a temperature of 5° C. diazotization was effected with 8.8 g of $NaNO_2$ dissolved in 41 ml of water. To the diazonium salt solution 20 g (0.117 mole) of 1,2-dihydro-1,2,2,4-tetramethyl-quinoline in a mixture of 500 ml of acetic acid, 40 ml of water and 85 g of sodium acetate were added.

The reaction mixture was stirred for 2 h and thereupon 1000 ml of water were added. The obtained azo compound was extracted with ethyl acetate. After evaporating the solvent 13.6 g of crude product were obtained. Purification with column-chromatography yielded compound F with melting point 72° C.

PREPARATION OF COMPOUND G

A mixture of 72.4 g (0.4 mole) of 2-amino-fluorene, 91.4 ml (0.8 mole) of mesityl oxide and 6.35 g (0.03 mole) of p-tolusulphonic acid were heated while distilling off acetone produced in the reaction. Duration about 3 h at 80°-84° C. Thereupon the temperature was raised till 105°-110° C. and at that temperature the reaction mixture was kept for 2 h. After cooling 150 ml of acetonitrile and 50 ml of water were added. The precipitate was separated by filtration and washed with a 3/1 by volume mixture of acetonitrile/water. Yield after drying 47 g. Melting point: 169° C.

PPREPARATION OF COMPOUND H

A suspension of 10.75 g (0.05 mole) of 1,2-dihydro-1,2,2,4-tetramethyl-6-formyl-quinoline. 11.1 g (0.05 mole) of N,N-diphenyl-hydrazine hydrochloride and 4.1 g (0.05 mole) of sodium acetate in 100 ml of ethanol were stirred for 2 h at 30°-40° C.

The reaction mixture was poured into 200 ml of water and the precipitate was separated by filtration. After purification by column-chromatogaphy 11 g of compound H were obtained. Melting point: 156 ° C.

PREPARATION OF COMPOUND J

A mixture of 7.10 g (0.033 mole) of 1,2-dihydro-1,2,2,4-tetramethyl-6-formyl-quinoline, 8.51 g (0.033 mole) of 4-(N-carbazolyl)-aniline and 350 ml of tolusulphonic acid were heated at reflux temperature while removing the water formed in the reaction by azeotropic distillation. The residual toluene was evaporated and the oily residue left was crystallized from 400 ml of acetonitrile. Yield: 13.1 g. Melting point: 177° C.

Duplo compounds for use according to the present invention are prepared advantageously by linking together by alkylation two 1,2-dihydroquinolines through their ring nitrogen atoms.

As suitable bifunctional alkylating agents are mentioned dihalogenated reactants that have the formula Hal-X-Hal in which Hal represents a replaceable halogen atom e.g. chlorine, bromine or iodine and X has the same significance as described above in the duplo-compounds.

The following are illustrative of reactants that may be used in the preparation of the duplo-compounds:
ethylene dichloride, dibromide, di-iodide and di-toluene sulfonate, 1-chloro-2-bromoethane, 1-chloro-ethane-2-toluene sulfonate, propylene dichloride, dibromide, di-iodide and di-toluene sulfonate, trimethylene dichloride, dibromide, bromoiodide and di-toluene sulfonate, butylene dichloride, dibromide, di-iodide, and di-toluene sulfonate, tetramethylene dichloride, dibromide, di-iodide, and di-toluene sulfonate. pentylene dichloride, dibromide, di-iodide, and di-toluene sulfonate. hexamethylene dichloride, dibromide, di-iodide, and di-toluene sulfonate, hexylene dichloride, dibromide, di-iodide, and di-toluene sulfonate, octylene dichloride, dibromide, di-iodide, and di-toluene sulfonate, pentamethylene dichlorde, dibromide, di-iodide, and di-toluene sulfonate, alpha, beta-styrene dichloride, dibromide, di-iodide, and di-toluene sulfonate,
1,2-dibromocyclohexane,
1,3-dibromobutane,
1,2-dibromobutane,
1,4-dichlorobutene,
2-phenyl-1,2-dibromopropane,
1-p-tolyl-1,2-dichloroethane,
1,4-di(chloromethyl)benzene, 1,2-di(chloromethyl)benzene, and
1,3-di(chloromethyl)benzene
1,3-di(bromomethyl)benzene, 1,2-di(bromomethyl)benzene, and
1,3-di(bromomethyl)benzene,
1,4(iodomethyl)benzene, 1,2-di(iodomethyl)benzene, and
1,3-di(iodomethyl)benzene,
1(b 2,4-dichlorophenyl)1,2-dichloroethane,
1-(p-chlorophenyl)-1,2-dibromethane,
decamethylene dichloride, dibromide, di-iodide and di-toluene sulfonate,
dodecamethylene dichloride, dibromide, di-iodide and di-toluene sulfonate,
1,2-dibromobutene-3,
1,2-dichloropentene-4,
1,2-dichloro-3-methylbutene-3,
1,4-dichlorobutene-2,
1,4-dibromo-2,3-dimethylbutene-2,
1,2-dichlorocyclopentene-3,
1,4-dibromo-2,6-dimethylheptene-2, and
2,3-dichloro-2,6-dimethyloctene-6.

Other suitable reactants for duplo-compound formation are the Beta-chloroethyl ester of p-toluenesulfonic acid and the p-toluenesulfonic acid glycol diester.

Preferred reactants are sym.-dibromoethane, sym.-dichloroethane and 1-chloro-ethane-2-toluenesulfonate.

The acid produced during the alkylation reaction may be neutralized by any alkaline neutralizing agent ordinarily employed for neutralizing acids produced in condensation reactions e.g. an organic base.

A detailed description of the preparation of most of the 1,2-dihydroquinoline compounds including the duplo-compounds is given in detail in U.S. Pat. No. 3,832,171.

The preparation of compound 12 (no. 12) being a new duplo compound proceeded according to the following reaction scheme:

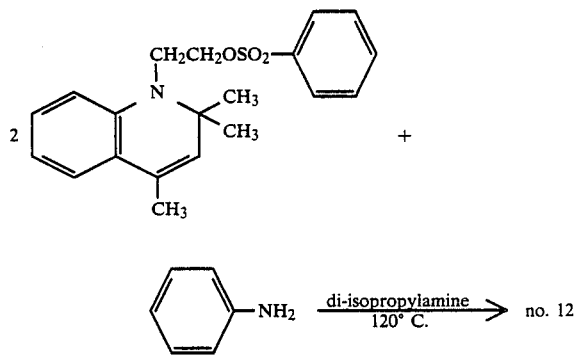

Said new compound no. 12 has photoconductive properties comparable with the 1,2-dihydroquinolines described in U.S. Pat No. 3,832,171 and may be used likewise in single photoconductive layer recording materials described therein.

For the production of a recording material according to the present invention at least one 1,2-dihydroquinoline compound according to general formula (I) is applied in combination with a resin binder to form a charge transporting layer adhering directly to a charge generating layer on an electrically conductive support. Through the resin binder the charge transporting layer obtains sufficient mechanical strength and obtains or retains sufficient capacity to hold an electrostatic charge for copying purposes. Preferably the specific resistivity of the charge transporting layer is not lower than $10^9$ ohm.cm. The resin binders are selected in view of optimal mechanical strength, adherence to the charge generating layer and favourable electrical properties.

Suitable electronically inactive binder resins for use in the charge transporting layer are e.g. cellulose esters, acrylate and methacrylate resins, e.g. cyanoacrylate resin, polyvinyl chloride, copolymers of vinyl chloride, e.g. copolyvinyl/acetate and copolyvinyl/maleic anhydride. polyester resins, e.g. copolyesters of isophthalic acid and terephthalic acid with glycol, aromatic polycarbonate resins and polyester carbonate resins.

A polyester resin particularly suited for use in combination with aromatic polycarbonate binders is DYNAPOL L 206 (registered trade mark of Dynamit Nobel for a copolyester of terephthalic acid and isophthalic acid with ethylene glycol and neopentyl glycol, the molar ratio of tere- to isophthalic acid being 3/2). Said polyester resin improves the adherence to aluminium that may form a conductive coating on the support of the recording material.

Suitable aromatic polycarbonates can be prepared by methods such as those described by D. Freitag. U. Grigo, P. R. Müller and W. Nouvertné in the Encyclopedia of Polymer Science and Engineering, 2nd ed., Vol. II, pages 648–718, (1988) published by Wiley and Sons Inc., and have one or more repeating units within the scope of the following general formula (III):

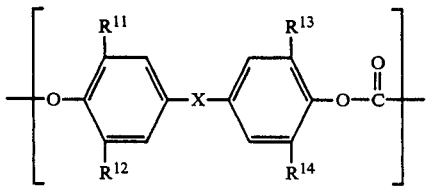

(III)

wherein:

X represents S, SO$_2$,

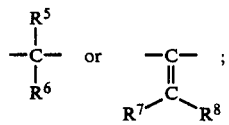

$R^{11}$, $R^{12}$, $R^{13}$, $R^{14}$, $R^7$ and and $R^8$ each represents (same or different) hydrogen, halogen, an alkyl group or an aryl group, and $R^5$ and $R^6$ each represent (same or different) hydrogen, an alkyl group, an aryl group or together represent the necessary atoms to close a cycloaliphatic ring, e.g. cyclohexane ring.

Aromatic polycarbonates having a molecular weight in the range of 10,000 to 200,000 are preferred. Suitable polycarbonates having such a high molecular weight are sold under the registered trade mark MAKROLON of Farbenfabriken Bayer AG, W-Germany.

MAKROLON CD 2000 (registered trade mark) is a bisphenol A polycarbonate with molecular weight in the range of 12,000 to 25,000 wherein $R_{11}=R^{12}=R^{13}=R^{14}=H$, X is $R^5$-C-$R^6$ with $R^5=R^6=CH_3$.

MAKROLON 5700 (registered trade mark) is a bisphenol A polycarbonate with molecular weight in the range of 50,000 to 120,000 wherein $R^{11}=R^{12}=R^{13}=R^{14}=H$, X is $R^5$-C-$R^6$ with $R^5=R^6=CH_3$.

Bisphenol Z polycarbonate is an aromatic polycarbonate containing recurring units wherein $R^{11}=R^{12}=R^{13}=R^{14}=H$, X is

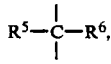

and $R^5$ together with $R^6$ represents the necessary atoms to close a cyclohexane ring.

Further useful binder resins are silicone resins, polystyrene and copolymers of styrene and maleic anhydride and copolymers of butadiene and styrene.

An example of an electronically active resin binder is poly-N-vinylcarbazole or copolymers of N-vinylcarbazole having a N-vinylcarbazole content of at least 40% by weight.

The ratio wherein the charge-transporting 1,2-dihydroquinoline compound and the resin binder are mixed can vary. However, relatively specific limits are imposed, e.g. to avoid crystallization. The content of the 1,2-dihydroquinoline used according to the present invention in a positive charge transport layer is preferably in the range of 30 to 70% by weight with respect to the total weight of said layer. The thickness of the charge transport layer is in the range of 5 to 50 μm, preferably in the range of 5 to 30 μm.

The presence of one or more spectral sensitizing agents can have an advantageous effect on the charge transport. In that connection reference is made to the methine dyes and xanthene dyes described in U.S. Pat. No. 3,832,171. Preferably these dyes are used in an amount not substantially reducing the transparency in the visible light region (420-750 nm) of the charge transporting layer so that the charge generating layer still can receive a substantial amount of the exposure light when exposed through the charge transporting layer.

The charge transporting layer may contain compounds substituted with electron-acceptor groups forming an intermolecular charge transfer complex, i.e. donor-acceptor complex wherein the 1,2-dihydroquinoline represents a donor compound by the presence of its electron donating aliphatically substituted ring nitrogen. Useful compounds having electron-accepting groups are nitrocellulose and aromatic nitro-compounds such as nitrated fluorenone-9 derivatives, nitrated 9-dicyanomethylenefluorenone derivatives, nitrated naphthalenes and nitrated naphthalic acid anhydrides or imide derivatives. The optimum concentration range of said derivatives is such that the molar donor/acceptor ratio is 10:1 to 1.000:1 and vice versa.

Compounds acting as stabilising agents against deterioration by ultra-violet radiation, so-called UV-stabilizers, may also be incorporated in said charge transport layer. Examples of UV-stabilizers are benztriazoles.

For controlling the viscosity of the coating compositions and controlling their optical clarity silicone oils may be added to the charge transport layer.

The charge transport layer used in the recording material according to the present invention possesses the property of offering a high charge transport capacity coupled with a low dark discharge. While with the common single layer photoconductive systems an increase in photosensitivity is coupled with an increase in the dark current and fatigue such is not the case in the present double layer arrangement wherein the functions of charge generation and charge transport are separated and a photosensitive charge generating layer is arranged in contiguous relationship to a charge transporting layer.

As charge generating compounds for use in a recording material according to the present invention any of the organic pigment dyes belonging to one of the classes (a) to (n) mentioned hereinbefore may be used. Further examples of pigment dyes useful for photogenerating positive charge carriers are disclosed in U.S. Pat. No. 4,365,014.

Inorganic substances suited for photogenerating positive charges in a recording material according to the present invention are e.g. amorphous selenium and selenium alloys e.g. selenium-tellurium, selenium-tellurium-arsenic and selenium-arsenic and inorganic photoconductive crystalline compounds such as cadmium sulphoselenide, cadmiumselenide, cadmium sulphide and mixtures thereof as disclosed in U.S. Pat. No. 4,140,529.

Said photoconductive substances functioning as charge generating compounds may be applied to a support with or without a binding agent. For example, they are coated by vacuum-deposition without binder as described e.g. in U.S. Pat. Nos. 3,972,717 and 3,973,959. When dissolvable in an organic solvent the photoconductive substances may likewise be coated using a wet coating technique known in the art whereupon the solvent is evaporated to form a solid layer. When used in combination with a binding agent or agents at least the binding agent(s) should be soluble in the coating solution and the charge generating compound dissolved or dispersed therein. The binding agent(s) may be the same as the one(s) used in the charge transport layer which normally provides best adhering contact. In some cases it may be advantageous to use in one or both of said layers a plasticizing agent, e.g. halogenated paraffin, polybiphenyl chloride, dimethylnaphthalene or dibutyl phthalate.

The thickness of the charge producing layer is preferably not more than 10 μm, more preferably not more than 5 μm.

In the recording materials of the present invention an adhesive layer or barrier layer may be present between the charge generating layer and the support or the charge transport layer and the support. Useful for that purpose are e.g. a polyamide layer, nitrocellulose layer, hydrolysed silane layer, or aluminium oxide layer acting as blocking layer preventing positive or negative charge injection from the support side. The thickness of said barrier layer is preferably not more than 1 micron.

The conductive support may be made of any suitable conductive material. Typical conductors include aluminum, steel, brass and paper and resin materials incorporating or coated with conductivity enhancing substances, e.g. vacuum-deposited metal, dispersed carbon black, graphite and conductive monomeric salts or a conductive polymer, e.g. a polymer containing quaternized nitrogen atoms as in Calgon Conductive polymer 261 (trade mark of Calgon Corporation, Inc., Pittsburgh, Pa., U.S.A.) described in U.S. Pat. No. 3,832,171.

The support may be in the form of a foil, web or be part of a drum.

An electrophotographic recording process according to the present invention comprises the steps of:

(1) overall negatively electrostatically charging, e.g. with corona-device, the charge transporting layer or charge generating layer of the recording material of the present invention, (2) image-wise photo-exposing the charge generating layer of the recording material according to the present invention thereby obtaining a latent electrostatic image.

The photo-exposure of the charge generating layer proceeds preferably through the charge transporting layer but may be direct if the charge generating layer is uppermost or may proceed likewise through the conductive support if the latter is transparent enough to the exposure light.

The development of the latent electrostatic image commonly occurs preferably with finely divided electrostatically attractable material, called toner particles that are attracted by coulomb force to the electrostatic charge pattern. The toner development is a dry or liquid toner development known to those skilled in the art.

In positive-positive development toner particles deposit on those areas of the charge carrying surface which are in positive-positive relation to the original image. In reversal development, toner particles migrate and deposit on the recording surface areas which are in negative-positive image value relation to the original. In the latter case the areas discharged by photo-exposure obtain by induction through a properly biased developing electrode a charge of opposite charge sign with respect to the charge sign of the toner particles so that the toner becomes deposited in the photo-exposed areas that were discharged in the imagewise exposure (ref.: R. M. Schaffert "Electrophotography"-The Focal Press-London, New York, enlarged and revised edition 1975, p. 50–51 and T. P. Maclean "Electronic Imaging" Academic Press-London, 1979, p. 231).

According to a particular embodiment electrostatic charging, e.g. by corona, and the imagewise photo-exposure proceed simultaneously.

Residual charge after toner development may be dissipated before starting a next copying cycle by overall exposure and/or alternating current corona treatment.

Recording materials according to the present invention depending on the spectral sensitivity of the charge generating layer may be used in combination with all kinds of photon-radiation, e.g. light of the visible spectrum, infra-red light, near ultra-violet light and likewise X-rays when electron-positive hole pairs can be formed by said radiation in the charge generating layer. Thus, they can be used in combination with incandescent lamps, fluorescent lamps, laser light sources or light emitting diodes by proper choice of the spectral sensitivity of the charge generating substance or mixtures thereof. For light in the spectral range beyond 800 nm e.g. naphthalocyanines having siloxy groups bonded to the central metal silicon can be used as charge generating substance (ref. published EP-A No. 0 243 205).

The toner image obtained may be fixed onto the recording material or may be transferred to a receptor material to form thereon after fixing the final visible image.

A recording material according to the present invention showing a particularly low fatigue effect can be used in recording apparatus operating with rapidly following copying cycles including the sequential steps of overall charging, imagewise exposing, toner development and toner transfer to a receptor element.

The following examples further illustrate the present invention. All parts, ratios and percentages are by weight unless otherwise stated.

The evaluations of electrophotographic properties determined on the recording materials of the following examples relate to the performance of the recording materials in an electrophotographic process with a reusable photoreceptor. The measurements of the performance characteristics were carried out as follows:

The photoconductive recording sheet material was mounted with its conductive backing on an aluminium drum which was earthed and rotated at a circumferential speed of 10 cm/s. The recording material was sequentially charged with a negative corona at a voltage of $-4.6$ kV operating with a corona current of about 1 μA per cm of corona wire. Subsequently the recording material was exposed (simulating image-wise exposure) with a light dose of monochromatic light obtained from a monochromator positioned at the circumference of the drum at an angle of 45° with respect to the corona source. The photo-exposure lasted 200 ms. Thereupon, the exposed recording material passed an electrometer probe positioned at an angle of 180° with respect to the corona source.

After effecting an overall post-exposure with a halogen lamp producing 27,000 mJ/m2 postioned at an angle of 270° with respect to the corona source a new copying cycle started.

Each measurement relates to 100 copying cycles in which 10 cycles without monochromatic light exposure are alternated with 5 cycles with monochromatic light exposure.

The charging level (CL) is taken as the average charging level over the 90th to 100th cycle, the residual potential (RP) as the residual potential over the 85th to 90th cycle, the % discharge as $$\frac{(CL - RP)}{CL} \times 100$$

and the fatigue (F) as the difference in residual potential in volts between RP and the average residual potential over the 10th to 15th cycle.

For a given corona voltage, corona current, separating distance of the corona wires to recording surface and drum circumferential speed the charging level CL is only dependent upon the thickness of the charge transport layer and its specific resistivity. In practice CL expressed in volts should be preferably $\geq 30$ d, where d is the thickness in $\mu m$ of the charge transport layer.

Under the applied exposure conditions, simulating practical copying conditions, and by using a charge transport layer in conjunction with a charge generating layer on the basis of X-phthalocyanine as the charge generating pigment, the % discharge should be at least 35% and preferably at least 50%. The fatigue F should preferably not exceed 20 V either negative or positive to maintain a uniform image quality over a large number of copying cycles.

All ratios and percentages mentioned in the Examples are by weight.

EXAMPLE 1

A photoconductor sheet was produced by coating a 100 $\mu m$ thick polyester film vapour-coated with a conductive layer of aluminium with a dispersion of charge generating pigment to a thickness of 0.55 $\mu m$ with a doctor-blade coater.

Said dispersion was prepared by mixing 1 g of metal-free purified X-phthalocyanine, 0.1 g of a polyester adhesion-promoting additive DYNAPOL L 206 (registered trade mark), 0.9 g of aromatic polycarbonate MAKROLON CD 2000 (registered trade mark) and 23 g of dichloromethane for 20 minutes in a pearl mill, which dispersion before coating was diluted with 8 g of dichloromethane to the required coating viscosity.

The applied layer was dried for 15 minutes at 80° C. and then overcoated using a doctor-blade coater to a thickness of 12 $\mu m$ with a filtered solution of charge transporting material and binder consisting of 2 g of 1,2-bis-(1,2-dihydro-2,2,4-trimethylquinolin-1-yl)ethane (compound 1 of Table 2), b 2 g of MAKROLON CD 2000 (registered trade mark) and 26.6 g of dichloromethane. This layer was then dried for 1 hour at 80° C.

The characteristics of the thus obtained photoconductive recording material were determined with a light dose of 19.4 mJ/m2 of 650 nm light as described above with the following results:
CL = −814 V
RP = −298 V
% discharge = 63.4%
F = −13 V

EXAMPLE 2

A photoconductive recording sheet was produced as described in Example 1 except that the charge generating layer consisted of 50% of metal-free purified X-phthalocyanine in bisphenol Z polycarbonate [$R^{11}=R^{12}=R^{13}=R^{14}=H$; $X=R^5\text{-}C\text{-}R^6$ and $R^5+R^6=(CH_2)_5$-] and the charge transport layer consisted of 50% of compound 5 of Table 2 in MAKROLON 5700 (registered trade mark).

The characteristics of the thus obtained photoconductive recording material were determined with a light dose of 19.4 mJ/m2 of 650 nm light as described above with the following results:
CL = −353 V
RP = −124 V
% discharge = 64.9%
F = −34 V

EXAMPLES 3 to 20

Photoconductive recording sheets were produced as described in Example 1 except that the charge transport layer consisted of the charge transport compound given in Table 3 hereinafter for the respective example in MAKROLON CD 2000 (registered trade mark). The characteristics of this photoconductive recording sheet were determined with a light dose of 19.4 mJ/m2 of 650 nm light as described above. In said Table 3 the results are given together with the charge transport compound concentration.

TABLE 3

| Example No. | Charge transport compound | Charge transport compound conc. in wt % | CL [V] | RP [V] | % Discharge | F [V] |
|---|---|---|---|---|---|---|
| 3 | A | 50 | −622 | −226 | 63.6 | −42 |
| 4 | B | 50 | −724 | −342 | 52.8 | +3 |
| 5 | C | 50 | −739 | −528 | 28.5 | −80 |
| 6 | D | 50 | −779 | −463 | 40.6 | −56 |
| 7 | E | 50 | −670 | −330 | 50.7 | +9 |
| 8 | G | 50 | −570 | −330 | 42.1 | −5 |
| 9 | H | 50 | −691 | −294 | 57.4 | +58 |
| 10 | I | 50 | −611 | −281 | 54.0 | +65 |
| 11 | J | 50 | −609 | −456 | 25.1 | +138 |
| 12 | 4 | 30 | −628 | −289 | 54.0 | +10 |
| 13 | 7 | 50 | −652 | −285 | 56.3 | −35 |
| 14 | 8 | 40 | −746 | −364 | 51.2 | −3 |
| 15 | 9 | 50 | −791 | −373 | 52.8 | −5 |
| 16 | 10 | 50 | −755 | −250 | 66.9 | +23 |
| 17 | 12 | 50 | −769 | −403 | 47.6 | +8 |
| 18 | 13 | 50 | −689 | −261 | 62.1 | +10 |
| 19 | 14 | 50 | −561 | −250 | 55.4 | +32 |
| 20 | 15 | 50 | −626 | −269 | 57.0 | +38 |

EXAMPLES 21 to 33

Photoconductive recording sheets were produced as described in Examples 20 to 24 except that the charge transport layer consisted of the charge transport compound given in Table 4 for the respective in MAKROLON CD 2000 (registered trade mark).

The characteristics of these recording sheets were determined with a light dose of 8.5 mJ/m2 of 540 nm light as described above. The results are given together with the charge transport compound concentration in

TABLE 4

| Example No. | Charge transport compound | Charge compound conc. in wt % | CL [V] | RP [V] | % Discharge | F [V] |
|---|---|---|---|---|---|---|
| 21 | A | 50 | −635 | −270 | 57.5 | −6 |
| 22 | C | 50 | −859 | −688 | 19.9 | −111 |
| 23 | D | 50 | −769 | −521 | 32.2 | −64 |
| 24 | E | 50 | −739 | −401 | 45.7 | −18 |
| 25 | H | 50 | −620 | −218 | 64.8 | −5 |
| 26 | I | 50 | −127 | −35 | 72.4 | −1 |
| 27 | 1 | 50 | −855 | −375 | 56.1 | +3 |
| 28 | 4 | 30 | −758 | −426 | 43.8 | −12 |
| 29 | 7 | 50 | −675 | −333 | 50.7 | −7 |
| 30 | 10 | 50 | −788 | −437 | 44.5 | −15 |
| 31 | 13 | 50 | −803 | −457 | 43.1 | −24 |
| 32 | 14 | 50 | −736 | −393 | 46.6 | −6 |
| 33 | 15 | 50 | −738 | −404 | 45.3 | −10 |

EXAMPLE 34

A photoconductive recording sheet was produced is described in Example 1 except that the charge carrier generating layer consisted of 50% metal-free purified X-phthalocyanine, 5% of a polyester adhesion-promoting additive and 45% of poly[bis-1,1'-(4-hydroxy-3,5-dimethylphenyl)-2-propyl-carbonate] and the charge carrier transport layer consisted of 50% of compound 1 of Table 2 in poly[bis-1,1'-(4-hydroxy-3,5-dimethylphenyl)-2-propyl-carbonatel. The characteristics of this photoconductive recording sheet were determined with a light dose of 19.4 mJ/m2 of 650 nm light as described above with the following results:

CL = −768 V
RP = −305 V
% discharge = 60.3%
F = +9 V

EXAMPLE 35

A photoconductive recording sheet was produced as described in Example 1 except that the charge carrier generating layer consisted of 50% metal-free purified X-phtalocyanine. 10% of the polyester adhesion-promoting additive DYNAPOL L 206 (trade name) and 40% of poly[bis-1,1'-(b 4-hydroxyphenyl)-1-phenylethane-carbonate] and the charge carrier transport layer consisted of 50% of compound 1 of Table 2 in poly[bis-1.1'-(4-hydroxyphenyl)-1-phenylethane-carbonate].

Said polymer having a weight averaged molecular weight of 36,900 and a number averaged molecular weight of 15,000.

The characteristics of this photoconductive recording layer were determined with a light dose of 19.4 mJ/m2 of 650 nm light as described above with the following results:

CL = −636 V
RP = −190 V
% discharge = 70.1%
F = −10 V

EXAMPLE 36

A photoconductive sheet was produced as described in Example 1 except that the charge carrier generating layer consisted of 50% metal-free X-phthalocyanine, 5% of a polyester adhesion-promoting additive and 45% of poly[bis-1,1'-(4-hydroxyphenyl)-diphenylmethane-carbonate] and the charge carrier transport layer consisted of 50% of compound 1 of Table 2 in poly[bis-1,1'-(4-hydroxyphenyl)-diphenylmethane-carbonate].

The characteristics of this photoconductive recording sheet were determined with a light dose of 19.4 mJ/m2 of 650 nm light as described above with the following results:

CL = −773 V
RP = −357 V
% discharge = 53.8
F = −11 V

EXAMPLE 37

A photoconductive sheet was produced as described in Example 1 except that the charge carrier generating layer consisted of 50% metal-free X-phthalocyanine, 5% of a polyester adhesion-promoting additive and 45% of a copolymer of [bis-1,1'-(4-hydroxy-3,5-dimethylphenyl)-2-propyl-carbonate] and bis-1,1'-(4-hydroxyphenyl)-2-propyl-carbonatel and the charge carrier transport layer consisted of 50% of compound 1 of Table 2 in a copolymer of [bis-1,1'-(4-hydroxy-3,5-dimethylphenyl)-2-propyl-carbonate] and (bis-1,1'-(4-hydroxyphenyl)-2-propyl-carbonate].

The characteristics of this photoconductive recording sheet were determined with a light dose of 19.4 mJ/m2 of 650 nm light as described above with the following results:

CL = −810 V
RP = −318 V
% discharge = 60.7
F = +6 V

EXAMPLE 38

A photoconductive sheet was produced as described in Example 1 except that the charge carrier generating layer consisted of 50% metal-free X-phthalocyanine. 5% of a polyester adhesion-promoting additive and 45% of a polyester carbonate with 20 mol % bisphenol A carbonate and 80 mol % of a 1:1 mixture of terephthalate and isophthalate-bisphenol A ester. The charge carrier transport layer consisted of 50% of compound 1 of Table 2 in the above-mentioned copolymer.

The characteristics of this photoconductive recording sheet were determined with a light dose of 19.4 mJ/m2 of 650 nm light as described above with the following results:

CL= −668 V
RP= −288 V
% discharge=56.9
F= +11 V

EXAMPLE 39

Example 39 was produced by first doctor-blade coating a 100 um thick polyester film precoated with a vacuum-deposited conductive layer of aluminium with a 1% solution of γ-aminopropyltriethoxy silane in aqueous methanol. After solvent evaporation and curing at 100° C. for 30 minutes, the thus obtained adhesion/blocking layer was doctor-blade coated with a filtered solution of charge transporting material and binder consisting of 3 g of 1,2-bis-(1,2-dihydro-2,2,4-trimethyl-quinolin-1-yl) ethane, 3 g of MAKROLON 5700 (registered trade mark) and 44 g of dichloromethane to a thickness of about 15 μm.

After drying for 15 minutes at 50° C. this layer was coated with a dispersion of charge generating pigment to a thickness of 5 μm.

Said dispersion was prepared by mixing 1.0 g of metal-free X-phthalocyanine, 1.0 g of 1.2-bis(1,2-dihydro-2,2,4-trimethyl-quinolin-1-yl) ethane. 1.33 g of MAKROLON CD 2000 and 24.4 g of dichloromethane for 15 minutes in pearl mill. Subsequently the dispersion was diluted with 5.55 g of dichloromethane to the required coating viscosity. The layer was then dried at 50° C. for 16 hours.

The characteristics of the thus obtained photoconductive recording material were determined with a light dose of 19.4 mJ/m2 of 650 nm light as described above except that the said material was positively charged rather than negatively charged. The results were as follows:

CL= +716 V
RP= +177 V
% discharge=75.3
F= +15 V

We claim:

1. An electrophotographic recording material which comprises an electrically conductive support having thereon a charge generating layer in contiguous relationship with a charge transporting layer, wherein said charge transporting layer contains a 1,2-dihydroquinoline compound corresponding to the following general formula(I):

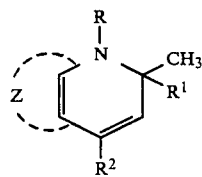

wherein:
R represents hydrogen or an aliphatic or cycloaliphatic group including these groups substituted by non-ionic substituents. each of $R^1$ and $R^2$ (same or different) represents a $C_1$–$C_6$ alkyl group or an aryl group, and
Z represents the atoms necessary to close an adjacent aromatic nucleus or aromatic ring system including such nucleus or ring system substituted with one or more substituents of non-ionic character.

2. An electrophotographic recording material according to claim 1, wherein the compound according to general formula (I) has a melting point of at least 100° C.

3. An electrophotographic recording material according to claim 1. wherein R represents an alkyl group or substituted alkyl group introduced by alkylation.

4. An electrophotographic recording material according to claim 1, wherein R represents a benzyl group.

5. An electrophotographic recording material according to claim 1, wherein said 1,2-dihydroquinoline compound is a compound within the scope of the following general formula (II):

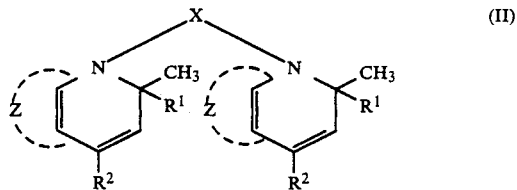

wherein:
X is a bivalent aliphatic or cycloaliphatic group, and $R^1$, $R^2$ and Z have the same significance as described in claim 1.

6. An electrophotographic recording material according to claim 5, wherein X represents a bivalent hydrocarbon group of the type that can be introduced by alkylation.

7. An electrophotographic recording material according to claim 5, wherein X represents an alkylene group including a substituted alkylene group or an alkylene chain interrupted by a bivalent aromatic group or a bivalent aliphatic group wherein at least two carbon atoms are linked through a hetero-atom selected from the group consisting of oxygen, sulphur or nitrogen wherein nitrogen is substituted with a monovalent hydrocarbon group.

8. An electrophotographic recording material according to claim 1, wherein said 1,2-dihydroquinoline compound is applied in combination with a resin binder to form a charge transporting layer adhering directly to said positive charge generating layer with one of the two layers being itself carried by an electrically conductive support.

9. An electrophotographic recording material according to claim 8, wherein the resin binder is selected from the group consisting of a cellulose ester, acrylate or methacrylate resin, polyvinyl chloride, copolymer of vinyl chloride, polyester resin, an aromatic polycarbonate resin, an aromatic polyester carbonate resin, silicone resin, polystyrene, a copolymer of styrene and maleic anhydride, a copolymer of butadiene and styrene, poly-N-vinylcarbazole and a copolymer of N-vinylcarbazole having a N-vinylcarbazole content of at least 40% by weight.

10. An electrophotographic recording material according to claim 8, wherein the content of said 1,2-dihydroquinoline in the positive charge transport layer is in the range of 30 to 70 by weight with respect to the total weight of said layer.

11. An electrophotographic recording material according to claim 1, wherein the charge generating layer contains for photo-induced electron-positive hole pair formation an organic substance selected from the group consisting of:
- (a) perylimides,
- (b) polynuclear quinones,
- (c) quinacridones,
- (d) naphthalene 1,4,5,8 tetracarboxylic acid derived pigments.
- (e) phthalocyanines,
- (g) benzothioxanthene-derivatives,
- (h) perylene 3,4,9,10-tetracarboxylic acid derived pigments,
- (i) polyazo pigments, and
- (j) squarilium dyes,
- (k) polymethine dyes,
- (l) dyes containing quinazoline groups,
- (m) triarylmethane dyes, and
- (n) dyes containing 1,5-diamino-anthraquinone groups.

12. An electrophotographic recording material according to claim 1, wherein the conductive support is made of aluminium, steel, brass or paper or resin material incorporating or being coated with a conductivity enhancing substance, the support being in the form of a foil, web or being part of a drum.

* * * * *